United States Patent

Nuckols et al.

Patent Number: 6,120,530
Date of Patent: Sep. 19, 2000

[54] PASSIVE THERMAL CAPACITOR FOR COLD WATER DIVING GARMENTS

[75] Inventors: Marshall L. Nuckols, Annapolis, Md.; Robert Hughes, Lynn Haven, Fla.; Cara Grupe, Oxford, United Kingdom; Steven W. Fitzgibbon, Panama City, Fla.

[73] Assignee: The United States of America as represented by the Secretary of the Navy, Washington, D.C.

[21] Appl. No.: 09/208,104

[22] Filed: Dec. 7, 1998

[51] Int. Cl.[7] ............................ B63C 11/04; B63C 11/02; A62B 17/00; A61F 7/00

[52] U.S. Cl. .................................. 607/108; 2/458; 2/2.15; 2/2.16; 405/186

[58] Field of Search ............................. 607/96, 114, 108; 441/102; 405/186; 2/2.14, 2.15, 457, 458, 2.11, 2.16

[56] References Cited

U.S. PATENT DOCUMENTS

| | | | |
|---|---|---|---|
| 3,449,761 | 6/1969 | Long ............................................. | 2/2.1 |
| 3,884,216 | 5/1975 | McCartney ............................... | 126/204 |
| 4,274,759 | 6/1981 | Long et al. ............................... | 405/186 |
| 4,503,850 | 3/1985 | Pasternak ........................... | 128/201.25 |
| 4,856,294 | 8/1989 | Scaringe et al. ........................... | 62/259 |
| 5,363,663 | 11/1994 | Chen ............................................ | 62/99 |
| 5,637,389 | 6/1997 | Colvin et al. ........................ | 428/308.4 |
| 5,984,953 | 11/1999 | Sabin et al. ............................... | 607/114 |

OTHER PUBLICATIONS http://www.thermasorb.com.

*Primary Examiner*—Linda C. M. Dvorak
*Assistant Examiner*—Jocelyn Debra Ram
*Attorney, Agent, or Firm*—Harvey A. Gilbert; Donald G. Peck

[57] ABSTRACT

A thermal liner in a diving suit has a layer of incompressible phase change materials for storing latent heat energy and for later releasing the stored energy while changing phase. This thermal liner provides thermal protection for divers' wetsuits, drysuits, and hot-water suits using stored energy from phase change materials, for extreme cold water diving. The thermal liner can function as an emergency backup heat source upon power failure when electrically-heated drysuits are used, or as an emergency backup heat source in case of interruption of warm water supply when hot-water diving suits are used. It can also be used as a supplemental source of heat for divers wearing passively-insulated wetsuits or drysuits to prolong acceptable durations in cold water missions. The thermal liner gives divers an emergency "come home" capability in case of power failure within drysuits supplied with an electrically-heated undergarment, or of an interruption of the warm water supply to a hot-water suit. A warm protective barrier is provided between the diver's skin and the hot-water suit that protects the diver from thermal shorts due to water current or compression of the suit by surface contacts. Alternately, the thermal liner may cool a diver during dressing on the surface by absorbing the diver's body heat as the phase change materials melt prior to the dive.

15 Claims, 2 Drawing Sheets

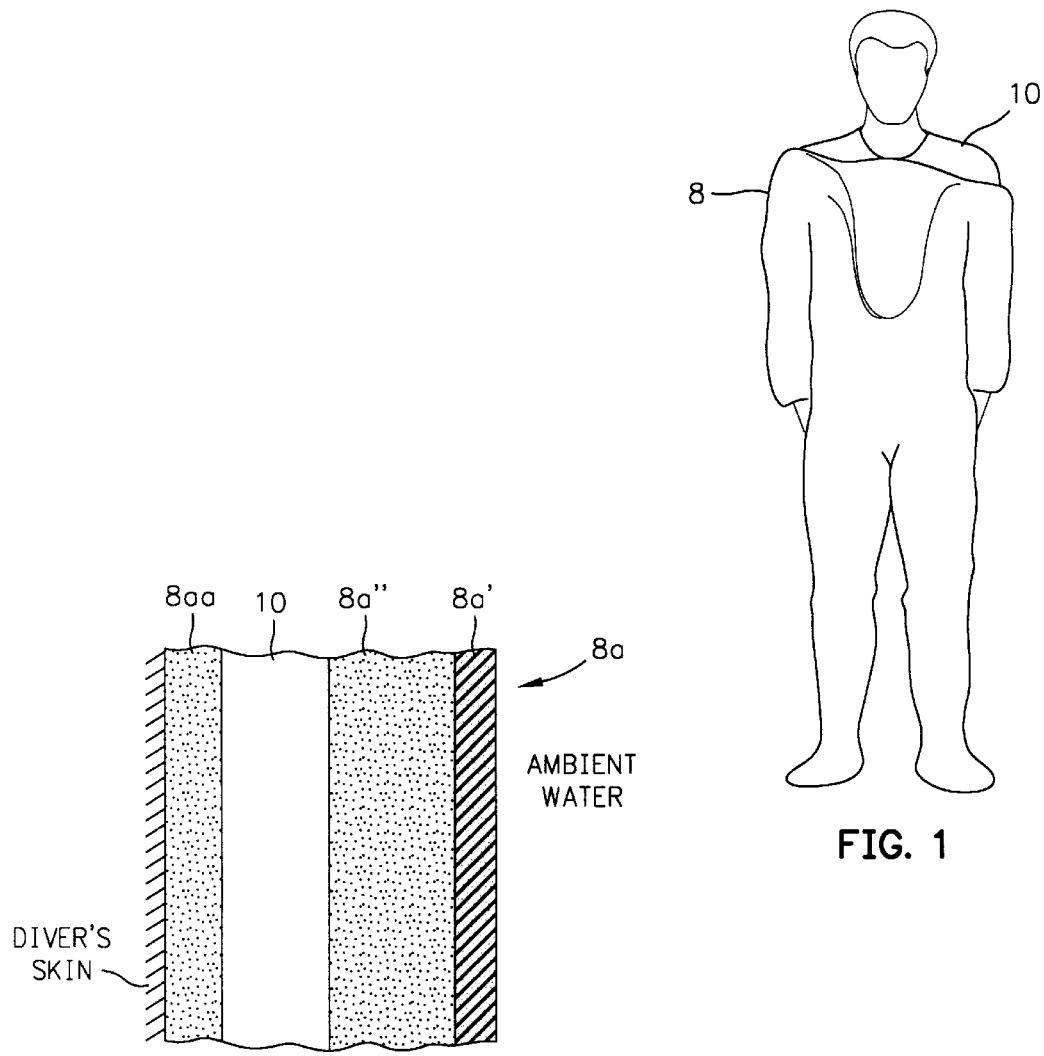
FIG. 1
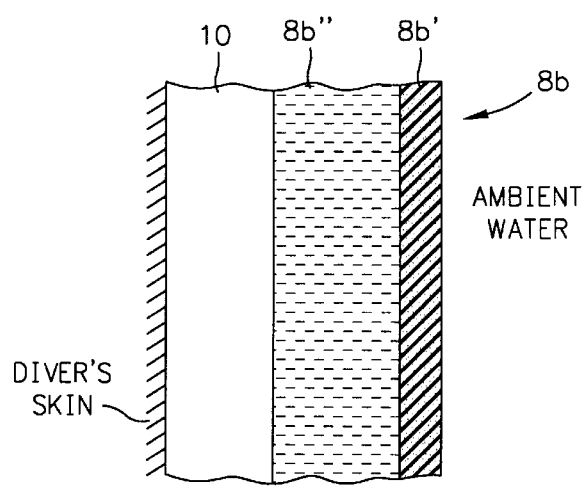
FIG. 2A
FIG. 2B

PASSIVE THERMAL CAPACITOR FOR COLD WATER DIVING GARMENTS

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

This invention relates to an improvement for diving suits. In particular, this invention relates to a thermal liner for diving suits that provides thermal protection using stored energy from phase change materials.

The rigors associated with diving are many. Surviving and capably functioning in the cold temperatures are problems as old as diving itself. Water conducts heat away from the human body 25 times faster in water than in air, and the heat capacity of water is greater than that of air by more than 3500 times. The significant difference between rates of heat loss at similar temperatures in air and when immersed in cold water creates a distinct difference in the physiological effects associated with the two. Immersion in extreme cold water incurs serious physiological effects that are potentially dangerous for a diver.

Consequently, several protective diving suits have evolved that make underwater tasks less difficult. Specifically, several forms of thermal protection systems exist to allow divers to operate safely when diving in severe cold environments. These include active heating systems that contain electrical resistive elements in the suit, or systems that provide a flow of warm water to a heat distribution garment worn by the diver. Unfortunately, both active heating systems offer negligible protection to the diver in the event of power failure to the electrically-heated suit, or interruption of water flow to the hot-water suit. Severe thermal stress to the diver can result without the presence of some type of emergency backup.

With the hot-water suit, warm water at approximately 100° F. is pumped into a loose outer garment to surround the diver with a layer of hot water for thermal protection. The hot water supply provides excellent thermal protection to divers in cold water as long as the water supply continues; however, the suit offers no real protection for a diver in an emergency when the supply of hot water is interrupted. Water temperatures in the suit have been shown to drop to dangerously low levels in just a few minutes after the cutoff of the hot water supply.

Wearing an electrically heated suit is not without its dangers. Interruption of power to the electrical suit can and does subject a diver to hazardous temperature conditions soon.

Besides the emergency situations described above, instances of cold water exposure sometimes occur during normal diving operations, even when the hot water flow is uninterrupted. Currently, divers wear conventional dive liners inside their hot-water suits; these dive liners prevent scalding of the divers if the temperature of the water entering the suits is too high. However, these liners do not offer any significant protection against cold in the event of water flow interruption. Additionally, in the midst of a mission, there are several causes of exposure to cold with the conventional liner even while the flow of hot water continues. The first of these occurs when the diver bends over or bends at the joints. In this situation, the joint presses against the outer garment of the loose fitting suit as the hot water is momentarily squeezed out of that particular area. This creates a "thermal short" which exposes an area of the diver to cold water exposure. Another instance in which cold water exposure routinely occurs is the performance of a mission in which the diver is standing in a water current. The current may push the suit against the diver's body, thus creating the same thermal short effect across even larger areas of a diver's body. The use of equipment that presses against the hot-water suit is another common way that body heat can pass from a diver.

Thus, in accordance with this inventive concept, a need has been recognized in the state of the art for overcoming the deficiencies of existing diving suits by providing a thin suit liner that contains stored energy in the form of latent heat that protects the diver against heat loss upon failure of the heat supply of the diving suit and is incompressible to prevent thermal shorts between the diver's skin and the diving suit.

SUMMARY OF THE INVENTION

The present invention is directed to providing an improvement for a diving suit. A thermal liner has at least a partial layer of incompressible phase change material that stores energy in the form of latent heat and releases the stored energy when it changes phase.

An object of the invention is to provide thermal protection for a diver.

Another object of the invention is to provide thermal liners for divers' wetsuits, drysuits, and hot-water suits that provide thermal protection, using stored energy from phase change material, for extreme cold water diving.

Another object of the invention is to provide an emergency backup heat source in case of interruption of warm water supply for divers wearing hot water diving suits.

Another object of the invention is to provide emergency backup heat source when power fails in electrically-heated drysuits.

Another object of the invention is to provide a supplemental source of heat for divers wearing passively-insulated wetsuits or drysuits to prolong acceptable durations for operations and missions in cold water.

Another object of the invention is to provide a backup thermal capacitor that continues to provide heat to the diver when power fails in an electrically-heated suit, or when the primary warm water supply is lost for a hot-water suit.

Another object of the invention is to provide diver cooling during dressing on the surface by absorbing the diver's body heat as the phase change material melts prior to the dive.

Another object of the invention is to provide a warm incompressible protective barrier between diver's skin and hot-water suit that protects the diver from thermal shorts due to water current or compression of the diving suit by surface contacts.

Still another object of the invention is to provide divers an emergency "come home" capability in case of power failure within drysuits supplied with an electrically-heated undergarment, or in case of interruption of the warm water supply to a hot-water suit.

These and other objects of the invention will become more readily apparent from the ensuing specification when taken in conjunction with the appended claims.

BRIEF DESCRIPTION OF THE DRAWINGS

FIG. 1 is a schematic drawing of a diver suiting-up in a drysuit over the PCM thermal liner of this invention.

FIGS. 2A and 2B schematically depict details of the thermal liner of this invention in an electrically heated drysuit and a hot-water suit, respectively.

DESCRIPTION OF THE PREFERRED EMBODIMENT

Figure 4A:
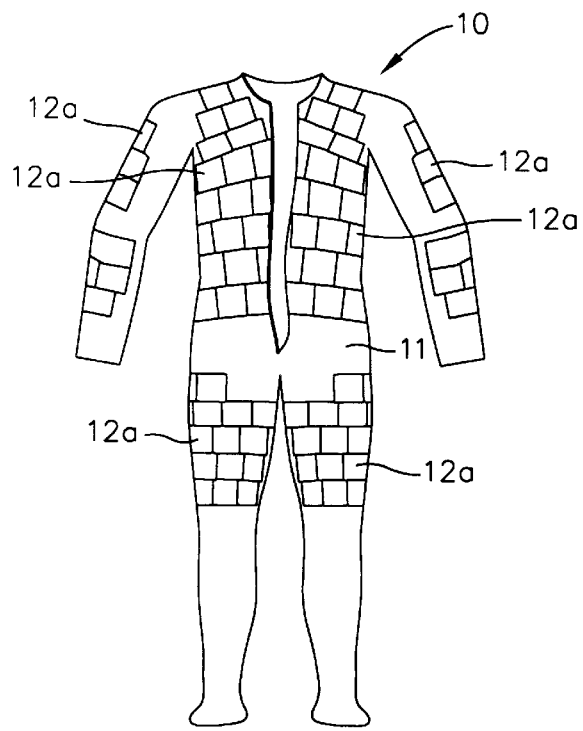
FIGS. 4A and 4B show one possible arrangement of pockets for PCM packets on the inside of the front and rear portions of the garment of PCM liner, respectively.

This invention creates a backup thermal capacitor which continues to provide a diver heat when power fails in an electrically-heated suit, or when the warm water supply is lost in a hot-water suit. This capacitor provides the diver with over 30 minutes of backup thermal protection after the loss of primary water supply to the hot-water suit. This protection gives the diver time to reach safety before water within the suit falls to dangerously low temperatures. Analysis shows that the same capacitor will give over 2 and ½ hours of protection when a diver uses an electrically-heated layer in a drysuit.

Referring to FIG. 1 of the drawings, a diver is shown before a dive while suiting-up in drysuit 8. Before drysuit 8 is put on, however, the diver dons form fitting thermal liner 10 of this invention. Thermal liner 10 has a flexible garment 11 that is designed to be worn next to the body and cover it much like a pair of close fitting long underwear. This garment 11 might preferably also be elastic so that it snugly fits while the diver bends and stretches performing the arduous tasks associated with diving operations. Neoprene, lycra, or sheet rubber might be suitable material for garment 11 and it is tailored to conform to the diver's body.

This fitting enables a close fit inside a diving suit, such as electrically heated drysuit 8a or hot-water suit 8b, shown in FIGS. 2A and 2B, respectively. The fit and constituency of thermal liner 10 assure that it provides increased thermal protection inside outer layer 8a' and insulation layer 8a" of drysuit 8a. Optionally, when extreme cold is expected, electrically heated layer 8aa can be worn between thermal liner 10 and the diver. Otherwise, thermal liner 10 is worn next to the diver's skin as shown in hot-water suit 8b. Thermal liner 10 fits next to the diver inside outer layer 8b' and hot-water layer 8b" of hot-water suit 8b.

Figure 3:
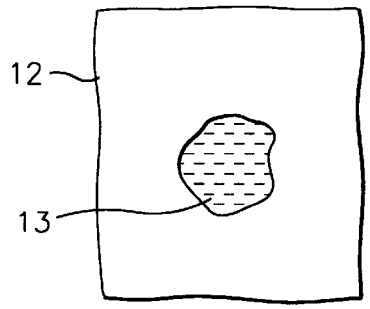
FIG. 3 shows a typical packet of phase change materials.

The reason that thermal liner 10 is so effective in protecting a diver from the consequences of exposure to the cold is that garment 11 is provided with many packets 12 containing phase change materials 13. FIG. 3 shows a typical packet 12, or PCM packet 12 of phase change materials 13 in the liquid phase. Each packet, or PCM packet 12 is a flat-shaped, flexible, plastic-like bag, measuring, for example, about 2 inches by 2 inches. Packets 12 containing phase change materials 13 may be put into and secured in suitably sized pockets 12 formed in garment 11, or packets 12 may be sewn into, bonded, or otherwise suitably affixed to garment 11.

Figure 4B:
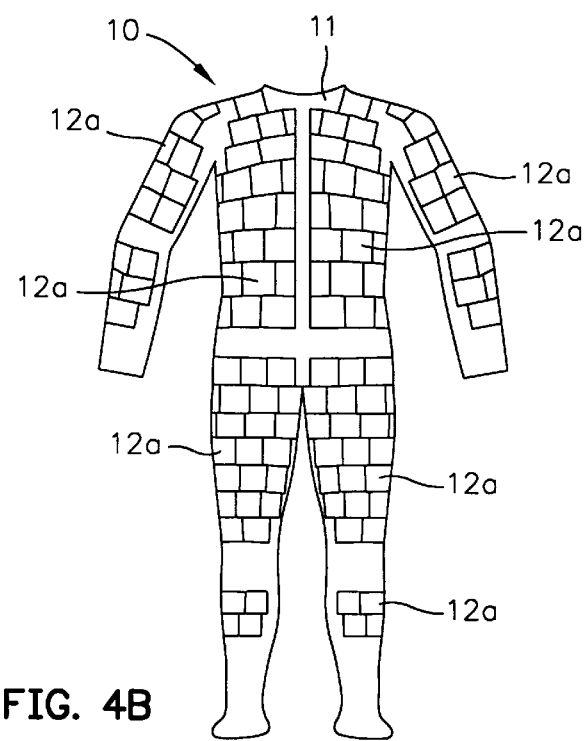

These packets 12 are arranged on garment 11 to cover major portions of a diver's body, particularly the major muscle groups or groups of muscles. FIGS. 4A and 4B depict one of many possible arrangements of pockets 12a on the inside of the front and rear portions of garment 11 of thermal, or PCM, liner 10 which cover groups of muscles of the arms, groups of muscles of the chest and stomach, groups of muscles of the back, groups of muscles of the buttocks and groups of muscles of the thighs and calves. Each pocket 12a has a separate PCM packet 12 inside of it. The arrangements of pockets 12a of packets 12 offer only scant restriction to the diver's range of motion or mobility.

Thermal liner 10 of this invention novelly incorporates phase change materials 13 in packets 12 to help protect a diver from undue exposure to cold water. Phase change material 13 has the unique, and desirable, characteristic of remaining at a constant temperature throughout the transition of the material from one physical phase to another.

This feature of phase change materials 13 is better realized by way of example. When hot water is flowing in hot-water diving suit 8b during a normal mission, phase change materials 13 in thermal liner 10 are converted into the liquid state while they store energy as latent heat. If the hot water supply is interrupted in water layer 8b", suit 8b loses temperature through conductive losses to ambient water. As the temperature drops, phase change materials 13 in thermal liner 10 cool. At their respective melting temperatures, phase change materials 13 undergo a phase change from liquid to solid form. Throughout this phase transition, phase change materials 13 remain at their respective melting temperatures until they lose quantities of heat equivalent to their latent heats of fusion. This thermal plateau of phase change materials 13 in thermal liner 10 is the factor that increases the duration of thermal protection for divers. Once this phase transition is complete, the temperature next to the diver's skin will begin to drop again at a steady rate as suit 8b further cools. Thermal liners 10 containing approximately 6 pounds of phase change materials 13 have held temperatures next to the diver's skin to within acceptable limits more than 30 minutes after the flow of warm water to a hot-water suit was interrupted. Analytical studies have shown that thermal liner 10 can provide over 2 and ½ hours protection to the diver when worn beneath drysuit 8a of FIG. 2A.

A number of suitable phase change materials are available. However, three representative phase change materials were selected from commercially available products. These representative products have slightly varying characteristics and are: (1) the phase microencapsulated phase-change materials commercially marketed by Frisby Technologies, Clemmons, N.C. 27102 under the trademark THERMASORB 98", (2) bulk octadecane with a melting temperature of approximately 83° F, and (3) bulk eicosane with a melting temperature of approximately 98° F. The phase change material of the trademark THERMASORB 98 consists primarily of eicosane that is microencapsulated in minuscule plastic beads. In recent cold water trials with the hot water suit, the eicosane liner maintained higher initial temperatures within the suit when the hot water supply was interrupted, but the octadecane liner appeared to give a more uniform suit temperature over the entire 30 minute period when the hot water was shut off. These results would indicate that the selection of the material used in liner 10 could be customized depending on what the primary mission may be; if maximum duration is desired, use one or more phase change materials in liner 10 having lower melting temperatures; if shorter durations are anticipated but higher suit temperatures are wanted, use one or more phase change materials with higher melting temperatures. Acceptable phase change materials 13 have melting temperatures between 83 and 98° F.

In accordance with this invention it is within the purview of one skilled in the art to select phase change materials to accommodate other uses. For example, a firefighter's protective suit may be provided with a liner having phase change materials that would cool the suit and the fireman. A suitable phase change material for such a suit might be hexadecane that melts at about 62° F.

Three thermal liners 10 using phase change materials 13 identified above also provided an incompressible warm protective barrier between the diver's skin and the hot-water suit. These incompressible thin-suit PCM liners 10 further protected divers from thermal shorts due to water currents or compression of the suit due to surface contacts. Additionally, all three liners 10 were observed to have negligible impact on the diver's mobility and/or range of motion.

Thermal liner 10 having phase change material 13 as herein described offers thermal capacitance inside wetsuits, hot-water suits and/or dry suits which gives divers an emergency "come home" capability. This capability could prove to be lifesaving upon power failure within drysuits supplied with an electrically-heated undergarment, or in case of interruption of the warm water supply to a hot-water suit. To reemphasize, thermal liner 10 also can provide a warm protective barrier between the diver's skin and the hot-water suit and also protects the diver from thermal shorts due to water current or compression of the suit due to surface contacts. A further use and advantage of thermal liner 10 is that it may cool the diver while dressing for the dive on the surface. This occurs by absorbing the diver's body heat as the phase change material 13 of liner 10 melts prior to the dive.

Another use of liner 10 is that it can also be used beneath passively-insulated wetsuits and drysuits to supplement the diver's thermal protection and to prolong acceptable durations in normal cold water missions. PCM liner 10 does this by producing its inherent thermal capacitance in these suits so that the diver does not suffer excessive heat loss through the diving suit. In these suits too, the incompressible nature of thermal liner 10 prevents thermal shorts due to contact between the diver's skin and the water when the diver presses against an object.

It should be readily understood that many modifications and variations of the present invention are possible within the purview of the claimed invention. It is therefore to be understood that within the scope of the appended claims the invention may be practiced otherwise than as specifically described.

We claim:

1. A thermal liner for a diving suit comprising:
   a close fitting flexible garment shaped to conform to a diver's body under a diving suit;
   a plurality of packets affixed to one side of said close fitting flexible garment, each of said packets being a flat flexible closed bag arranged in matrix-like patterns on said surface and said packets having their flat shapes covering major portions of said body; and
   incompressible phase change materials disposed in each of said flexible bags of said packets to store latent heat energy.

2. A thermal liner according to claim 1 further comprising:
   a plurality of pockets disposed on said surface of said close fitting flexible garment in said matrix-like patterns, each of said pockets containing a separate one of said packets of said phase change materials therein.

3. A thermal liner according to claim 2 in which said flexible garment is elastic to form-fit said diver, said pockets are secured to said surface of said garment, said pockets containing said packets of said incompressible phase change materials are sized to be small enough to require a plurality of said pockets to extend longitudinally across said surface in said matrix-like patterns and a plurality of said pockets to extend laterally across said surface in said matrix-like patterns.

4. A thermal liner according to claim 3 in which said packets are flexible plastic bags containing said phase change materials, and said major portions are where muscle groups are located.

5. A thermal liner according to claim 1, 2, 3, or 4 in which said phase change materials are selected from the group of thermal materials consisting of microencapsulated phase-change materials, bulk octadecane, and bulk eicosane.

6. A thermal liner according to claim 5 in which more than one of said group of thermal materials are combined to form said phase change materials.

7. A thermal liner according to claim 5 in which phase change of said phase change materials is from the solid phase to the liquid phase.

8. A thermal liner according to claim 5 in which phase change of said phase change materials occur in the range between 83 and 98° F.

9. A thermal liner according to claim 1, 2, 3, or 4 in which said diving suit is selected from the group consisting of hot-water suits, drysuits, and wetsuits.

10. An improved electrically heated drysuit comprising:
    an outer layer to contact ambient water;
    an insulating layer adjacent said outer layer;
    an electrically heated layer adjacent said insulating layer; and
    a thermal liner interposed between said insulating layer and said electrically heated layer, said thermal liner including;
    a close fitting flexible garment shaped to conform to a diver's body adjacent said heated layer;
    a plurality of packets affixed to one surface of said close fitting flexible garment, each of said packets being a flat flexible closed bag arranged in matrix-like patterns on said surface and said packets having their flat shapes covering major portions of said body;
    a plurality of pockets disposed on said surface of said close fitting flexible garment in said matrix-like patterns, each of said pockets containing a separate one of said packets therein;
    incompressible phase change materials disposed in each of said flexible bags of said packets to store latent heat energy, said pockets containing said packets of said incompressible phase change materials being sized to be small enough to require a plurality of said pockets to extend longitudinally across said surface in said matrix-like patterns and a plurality of said pockets to extend laterally across said surface in said matrix-like patterns.

11. A drysuit according to claim 10 in which said phase change materials are selected from the group of thermal materials consisting of microencapsulated phase-change materials, bulk octadecane, and bulk eicosane.

12. A drysuit according to claim 11 in which more than one of said group of thermal materials are combined as said phase change materials.

13. An improved hot water divine suit comprising:
    an outer layer to contact ambient water;
    a hot water layer adjacent said outer layer; and
    a thermal liner adjacent said hot water layer, said thermal liner including;
    a close fitting flexible garment shaped to conform to a diver's body under said hot water layer;
    a plurality of packets affixed to one surface of said close fitting flexible garment, each of said packets being a flat flexible closed bag arranged in matrix-like patterns on said surface and said packets having their flat shapes covering major portions of said body;
    a plurality of pockets disposed on said surface of said close fitting flexible garment in said matrix-like patterns, each of said pockets containing a separate one of said packets therein;

incompressible phase change materials disposed in each of said flexible bags of said packets to store latent heat energy, said pockets containing said packets of said incompressible phase change materials being sized to be small enough to require a plurality of said pockets to extend longitudinally across said surface in said matrix-like patterns and a plurality of said pockets to extend laterally across said surface in said matrix-like patterns.

14. A protective suit for a firefighter comprising:

a close fitting flexible garment conforming to a firefiahter's body;

a plurality of packets affixed to one surface of said close fitting flexible garment, each of said packets being a flat flexible closed bag arranged in matrix-like patterns on said surface and said packets having their flat shapes covering manor portions of said firefiahter's body;

a plurality of pockets disposed on said surface of said close fitting flexible garment in said matrix-like patterns, each of said pockets containing a separate one of said packets therein;

incompressible phase change materials disposed in each of said flexible bags of said packets to store latent heat energy, said phase change materials being hexadecane to release stored energy at 62° F., and said pockets containing said packets of said incompressible phase change materials being sized to be small enough to require a plurality of said pockets to extend longitudinally across said surface in said matrix-like patterns and a plurality of said pockets to extend laterally across said surface in said matrix-like patterns.

15. A thermal liner according to claim 1, 3, 10, 13, or 14 in which each flexible bag of said packets measures about two inches by two inches.

* * * * *